United States Patent [19]

Gauvry

[11] Patent Number: 5,417,646
[45] Date of Patent: May 23, 1995

[54] HIGH FLEXIBILITY KNEE SUPPORT

[75] Inventor: George R. Gauvry, Hainesport, N.J.

[73] Assignee: Cho-Pat, Inc., Hainesport, N.J.

[21] Appl. No.: 209,153

[22] Filed: Mar. 10, 1994

Related U.S. Application Data

[63] Continuation of Ser. No. 984,774, Dec. 3, 1992, abandoned.

[51] Int. Cl.$^6$ .............................. A61F 5/00
[52] U.S. Cl. ............................ 602/26; 602/62
[58] Field of Search ............... 602/62, 63, 23, 26; 128/882; 2/22, 24

[56] References Cited

U.S. PATENT DOCUMENTS

| | | | |
|---|---|---|---|
| 1,388,772 | 8/1921 | Sheehan | 602/63 |
| 2,179,903 | 11/1939 | Spears | 602/26 |
| 3,786,804 | 1/1974 | Lewis | 602/26 X |
| 3,945,046 | 3/1976 | Stromgren | 602/63 |
| 4,130,115 | 12/1978 | Taylor | 602/26 X |
| 4,296,744 | 10/1981 | Palumbo | 602/63 X |
| 4,370,978 | 2/1983 | Palumbo | 602/63 X |
| 4,423,720 | 1/1984 | Meier et al. | 602/62 X |
| 4,441,493 | 4/1984 | Nirschl | 602/62 |
| 4,748,975 | 6/1988 | Yashima | 602/62 X |
| 4,777,946 | 10/1988 | Watanabe et al. | 602/62 |
| 4,872,448 | 10/1989 | Johnson, Jr. | 602/26 |
| 5,016,621 | 5/1991 | Bender | 602/26 |
| 5,024,216 | 6/1991 | Shiono | 602/26 |
| 5,086,761 | 2/1992 | Ingram | 602/26 |
| 5,139,015 | 8/1992 | Morneau | 602/62 |
| 5,139,477 | 8/1992 | Peters | 602/62 X |

FOREIGN PATENT DOCUMENTS

8801855  3/1988  WIPO .................. 602/26

Primary Examiner—Linda C. M. Dvorak
Attorney, Agent, or Firm—Norman E. Lehrer; Jeffrey S. Ginsberg

[57] ABSTRACT

A high-flexibility knee support comprising a main body portion for covering the knee cap and surrounding area having securing straps extending from each side of the main body portion which are adapted to be wrapped around the knee and secured at the back of the knee. The straps are substantially less in width than the main body portion having straps for being secured comfortably and non-restrictively behind the knee. The knee support is further comprised of pressure-application straps which are attached to the main body portion above and below the knee cap. The pressure-application straps run from one side of the main body portion to the other side of the main body portion and are used to adjust the support given to the knee cap and patellar tendons. The adjusting straps can be adjusted and held in place via threading through rings attached to the main body portion and their construction from mating fractional fastening material, respectively.

13 Claims, 2 Drawing Sheets

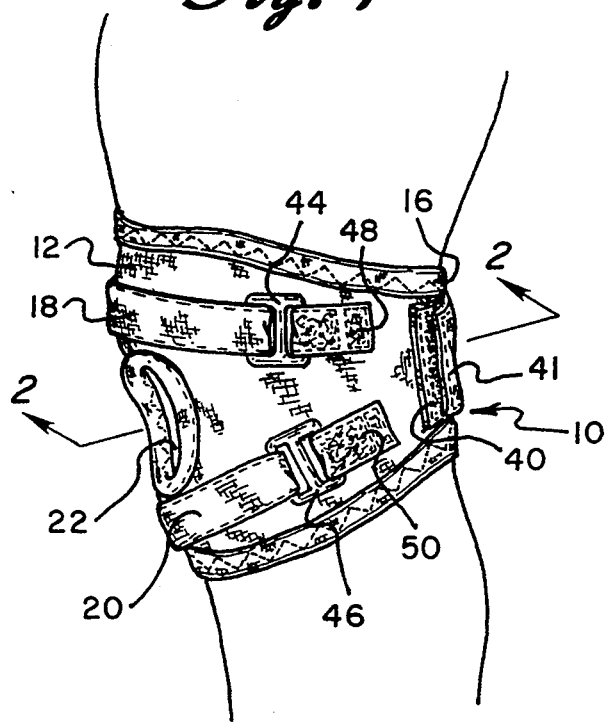
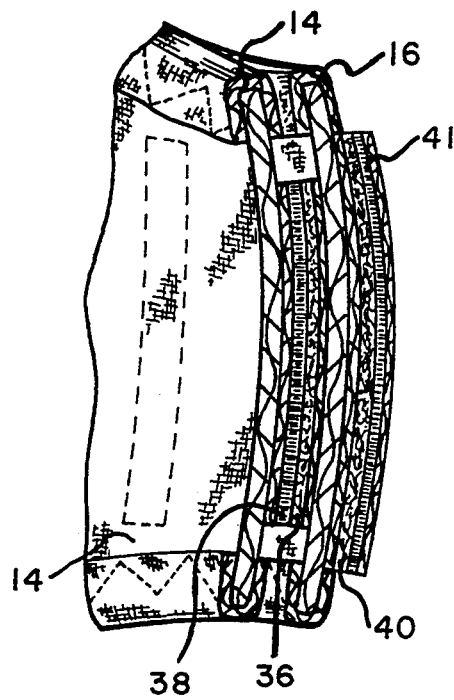
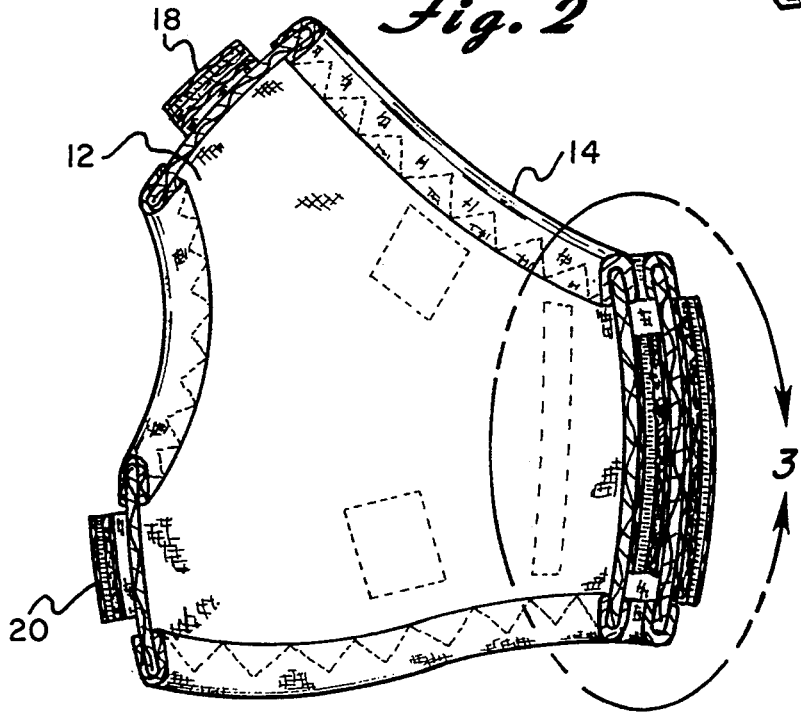

HIGH FLEXIBILITY KNEE SUPPORT

This is a continuation of prior application Ser. No. 984,774, filed Dec. 3, 1992, now abandoned.

BACKGROUND OF THE INVENTION

This invention relates generally to braces, and more particularly to a high-flexibility knee brace for supporting the patella and patellar tendons while still allowing unencumbered use of the knee.

Due to the knee being such a high-stress area, injuries to the knee and the surrounding area including the patella and patellar tendons are very frequent. As such, many braces have been designed and developed to give support to the knee and the surrounding area during exercise. Usually such a support is used after an injury to partially immobilize the weakened knee for preventing the possibility of further injury. Knee supports range in design from very small straps to highly involved and cumbersome rigid braces. The prior art discloses many knee brace designs which provide adequate support to the knee but fail to allow the user to move the knee in the desired or necessary fashion during certain exercises. In contradistinction, the less involved braces such as simple straps allow flexibility but don't supply the necessary support.

For example, U.S. Pat. No. 4,466,428 to McCoy, entitled "Patella Support Apparatus," discloses a relatively simple knee support for preventing lateral and medial movements of the patella. The apparatus is comprised of a rigid main body portion which fits over and around the knee, having an opening therethrough which exposes the knee cap. A strap extends from one side of the rigid member and is adapted to wrap around the leg and engage a ring extending from the other side of the rigid member. The apparatus provides support to the area surrounding the knee via tightening the strap through the ring.

U.S. Pat. No. 4,370,978 to Palumbo, entitled "Knee Brace," discloses a sleeve member for fitting over the knee wherein the sleeve member has an opening therethrough for exposing the knee cap. The sleeve member extends substantially above and below the knee cap. Toward the upper and lower ends of the sleeve member, straps are sewn which are adapted to encircle the areas substantially above and below the knee cap. The straps are adapted to be wrapped entirely around the leg and to be secured to the sleeve at the point from which they started for securing the brace to the leg. The sleeve has pads located on its interior surface running in a vertical direction to add additional support adjacent the knee cap.

A slightly more complex brace shown in U.S. Pat. No. 5,024,216 to Shiono, entitled "Knee Support," discloses a knee support comprising a main body designed to be wrapped substantially around the knee and secured thereto via a strap located above the knee cap and a strap located below the knee cap. The main body of the knee support extends substantially above the top of the knee cap and substantially below the bottom of the knee cap on the back and front side of the knee. Additional straps are located immediately above and below the area covering the actual knee cap. The straps extend to the interior of the brace and are connected to a pad used for providing lateral pressure to the patella. The straps are used to adjust the position and lateral pressure applied by the pad.

Finally, U.S. Pat. No. 4,287,885 to Applegate, entitled "Knee Brace With Resilient Pad Surrounding Patella," discloses an elastic-type sleeve being stretchable for placement around the patella and surrounding area. The interior surface is comprised of resilient pads arranged in a circular manner for surrounding the knee cap and providing pressure to the sides of the knee cap. The sleeve itself extends substantially above and below the knee cap. The resilient pads are maintained on a non-elastic sheet which is sewn to the elastic sleeve. Accordingly, the flexing of the knee during exercise and the subsequent stretching of material comprising the sleeve does not shift the resilient pads.

SUMMARY OF THE INVENTION

The invention described in this application is a high-flexibility knee support allowing the user of the support to maintain a high range of motion while still providing support and strength to the knee area.

In accordance with the invention, the high flexibility knee support comprises a flexible main body portion which covers the knee cap and the surrounding area and securing straps which extend from each side at the vertical center of the main body portion. The straps are wrapped around the knee area and have VELCRO attached thereto for attaching in the back of the knee and securing the knee support to the knee. The straps are substantially lesser in width than the main body portion to allow for comfort and high flexibility. The invention also includes means comprised of straps located on the main body portion above and below the knee cap area for applying pressure and adjusting the pressure to the patellar tendons.

The knee support is constructed primarily from a fabric-covered neoprene. The main portion and attached straps are formed substantially from the same piece of neoprene material. The main portion of the knee support which covers the knee cap and surrounding area has an opening therethrough for exposing the knee cap. The securing straps which extend from the main portion are adapted to engage behind the knee cap via mating VELCRO fastening material. In addition, a third VELCRO strap extends from one of the securing straps and is adapted for engaging mating VELCRO material located on the outer surface of the other securing strap.

The pressure applying means are comprised of straps located above and below the knee cap on the main body portion of the knee support. The straps are constructed from VELCRO fastening material such that the straps are capable of engaging themselves. The straps extend from one side of the main body portion to the other side of the main body portion to which rings are sewn. Pressure to the patellar tendons is adjusted by pulling the straps through the rings to the desired pressure and then fastening the strap to itself.

The knee support offers high flexibility along with the required support and comfort. As opposed to the prior art, this knee strap does not encumber the user during normal flexion of the knee in a variety of exercises yet still provides the necessary support. The knee support is used by simply placing it over the knee and surrounding area, securing it behind the knee via the securing straps and adjusting the pressure applied to the patellar tendons via the adjusting straps located on the main body portion.

DETAILED DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 shows the high-flexibility knee support being worn on the knee;

FIG. 2 is a cross-sectional view taken along line 2—2 of FIG. 1;

FIG. 3 is an exploded view of the area designated by line 3 in FIG. 2;

DETAILED DESCRIPTION OF THE PREFERRED EMBODIMENT

Figure 4:
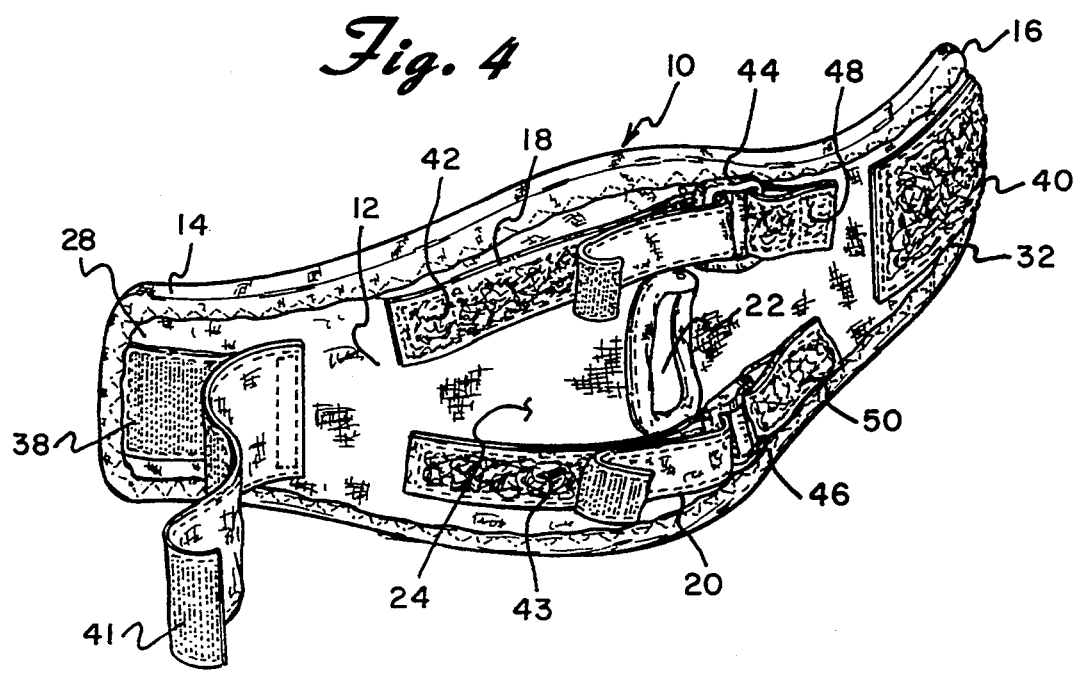
FIG. 4 is a front perspective view of the high-flexibility knee support.

Referring now to the drawings in detail wherein like reference numerals have been used throughout the various figures to designate like elements, there is shown in FIG. 4 a perspective view of the high-flexibility knee support constructed in accordance with the general principals of the present invention and designated generally as 10. The knee support 10 is comprised of a main body portion 12, securing straps 14 and 16 and pressure adjusting strap means 18 and 20. The securing straps 14 and 16 are an integral part of the main body portion 12. The pressure adjusting strap means 18 and 20 are secured to the front side of the main body portion extending from the left side of the main body portion to the right side of the main body portion.

In the preferred embodiment, the knee support is constructed from fabric-covered neoprene. It should be understood, however, that other materials may be used. Referring still to FIG. 4, the main body portion is substantially oval-shaped having an opening 22 in the center thereof for exposing the knee cap. The main body portion 12 is of substantially greater width (i.e. from top to bottom) than the securing straps 14 and 16. Accordingly, the straps 14 and 16 are of lesser width to allow ease of flexure of the knee during exercise and unencumbered movement. The straps fit non-restrictively into the area behind the knee on the back of the leg such that the person using the strap can function through almost the full range of his or her natural mobility.

The securing straps 14 and 16 are integral with the main body portion and extend from the center of the main body portion from the left and right sides thereof. The knee support may differ in size for different users, but the straps 14 and 16 should always be of sufficient length to be secured at the back of the leg for holding the knee support upon the knee. The securing straps hold the knee support to the leg by engaging each other. This can be accomplished in a number of ways but in a preferred embodiment, VELCRO strips are used on the straps such that mating VELCRO material is oppositely sewn to each strap.

Figure 5:
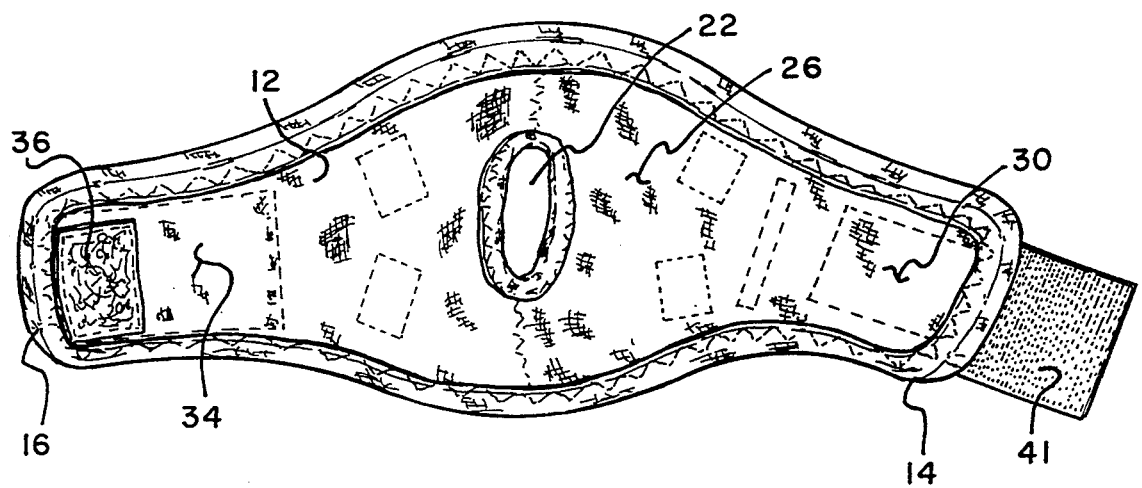
FIG. 5 is a rear perspective view of the high-flexibility knee support.

Referring now to FIGS. 4 and 5, the main body portion has a front side 24 and a back side 26 while the first securing strap 14 has a front side 28 and a back side 30 and the second securing strap 16 has a front side 32 and a back side 34. Mating VELCRO or frictional fastening material 36 and 38 are secured to the back side 34 of securing strap 16 and to the front side 28 of securing strap 14, respectively, such that upon securing the knee support to the knee, the first strap 14 is placed under the second strap 16 such that the VELCRO strips 36 and 38 engage and secure the knee support to the knee. In addition, VELCRO strip 40 is attached to the front side 32 of securing strip 16 while an additional mating VELCRO strap 41 extends from the front side 28 of securing strap 14. After being first secured via the VELCRO strips 36 and 38 as previously discussed, the knee support is given further security via the VELCRO strap 41 adhering to strap 16 and mating VELCRO material 40 as shown in FIG. 2 and 3.

The pressure adjusting strap means 18 and 20 similarly accomplish their purpose via the use of VELCRO or frictional fastening material although other methods may be used. There are two strap means, one strap means 18 located above the opening 22 through the main body portion and one strap means 20 located immediately below the opening 22. The strap means are comprised of straps 42 and 43, constructed from both materials required to form a VELCRO fastener, and rings 44 and 46. Strap 42 and strap 43 work in combination with rings 44 and 46, respectively, to accomplish the pressure-inducing function. Each ring 44 and 46 is secured to the main body portion via loops 48 and 50 fastened to the main body portion 12, respectively. Each pressure-adjusting strap 42 and 43 is adapted to be drawn through the rings 44 and 46, respectively, and fastened back to itself via the mating VELCRO material on the other half of each strap. The straps 42 and 43 and the pressure applied can be adjusted as desired by the user of the knee support.

The disclosed invention is used by exposing the knee and placing the knee support over the knee such that the opening 22 is centered upon the knee cap. The securing straps 14 and 16 are grasped by the user and pulled back towards and around the back side of the knee. The user of the knee support 10 should pull firmly on the securing straps 14 and 16 before securing the straps to each other via the mating VELCRO or frictional fastening material 38 and 36. The neoprene material is stretched so that the knee support is tightly secured to the knee area and then the mating VELCRO material should be engaged to secure the knee support to the knee. The VELCRO strap 41 is then secured to the opposing VELCRO material 40 on the other securing strap to provide additional security of the knee support to the knee area.

With the knee support securely fastened upon the knee, the pressure to the patellar tendons is adjusted as desired by use of the pressure-adjustment strap means 18 and 20. The straps 42 and 43 are threaded through the rings 44 and 46, respectively, as described and the straps are pulled until the desired pressure is given to the knee area. Upon reaching the desired pressure, each strap 42 and 43 is secured to itself toward its originating end via its composition from mating VELCRO material. The knee support 10 is now ready for use, allowing high flexibility while providing necessary support and comfort to the user.

The present invention may be embodied in other specific forms without departing from the spirit or essential attributes thereof and accordingly reference should be made to the appended claims rather than to the foregoing specification as indicating the scope of the invention.

What is claimed is:

1. A high flexibility knee support, comprising:

a main body portion adapted to substantially cover the area surrounding the knee cap;

securing straps extending from and attached to each side of said main body portion at substantially the vertical center of said main body portion, said straps being adapted to wrap around the knee area to the back of the knee, said straps having substantially lesser width than said main body portion and being adapted to fit comfortably and non-restrictively into the area behind the knee, said straps having means for securing said knee support to the knee;

said knee support further comprising pressure applying means distinct from the securing straps and main body portion but attached to said main body portion for applying direct pressure to the patellar tendons above and below the knee cap, said pressure applying means having means for adjusting the amount of pressure applied;

said pressure applying means comprising pressure strap and ring combination adapted to be located above and below the knee cap, each pressure strap and ring combination being attached to and extending from one side of said main body portion to the other side of said main body portion; and wherein said pressure adjustment means comprises each of said pressure straps adapted for being moved through the respective ring for said pressure strap and each of said pressure straps being comprised of mating hook and loop fastening material for securing each of said pressure straps to itself at the desired pressure after passing through said ring.

2. The invention according to claim 1 wherein said knee support has a first and a second securing strap, each of said securing straps having an inward and an outward facing surface, said securing means comprising mating hook and loop fastening material attached to said securing straps on the outward facing surface of said first securing strap and on the inward facing surface of said second securing strap.

3. The invention according to claim 2 wherein said securing means further comprises a third securing strap having a frictional fastening material surface and an additional frictional mating frictional fastening surface located on and attached to the outward facing surface of said second securing strap, said third securing strap being attached to and extending from the outward facing surface of said first strap and adapted to engage said additional mating surface for providing additional means for securing said support to the knee area.

4. The invention according to claim 1 wherein said main body portion has an opening therethrough for exposing the knee cap.

5. The invention according to claim 4 wherein said knee support is constructed from a fabric covered neoprene.

6. The invention according to claim 5 wherein said straps are integral parts of said main body portion.

7. The invention according to claim 1 wherein said pressure straps are adapted to extend along only the front portion of the knee.

8. A high flexibility knee support comprising:
a main body portion adapted to substantially cover the area surrounding the knee cap, said main body portion having a front and a back and first and second ends;
a first securing strap extending from said first end of said main body portion and a second securing strap extending from said second end of said main body portion, said straps being adapted to wrap around the knee area to the back of the knee, said straps each having a front and a back;
mating means for securing said first strap to said second strap;
pressure applying means distinct from said securing straps, said pressure applying means being secured only to said front of said main bodyportion for applying direct pressure to the patellar tendons above and below the knee cap, said pressure applying means extending substantially from said first end to said second end of said main body portion;
wherein said pressure applying means comprises a pair of spaced apart rings and first and second pressure straps, each of said pressure straps being adapted to pass through a corresponding ring, said first pressure strap being attached to the main body and adapted to be positioned above the knee cap when the knee support is in use, said second pressure strap being attached to the main body and adapted to be positioned below the knee cap when the knee support is in use, each of said pressure straps having means for adjusting the amount of pressure applied to the patellar tendons.

9. The invention according to claim 8 wherein said pressure adjusting means comprises said pressure straps having a plurality of hook fasteners secured to one end and a plurality of loop fasteners secured to the opposite end for securing each of said pressure straps to itself at a desired pressure after passing through a corresponding ring.

10. The invention according to claim 8 wherein said mating means comprises a plurality of loop fasteners secured to said back of said first strap and a plurality of hook fasteners secured to said front of said second strap.

11. The invention according to claim 10 wherein said main body portion has an opening therethrough for exposing the knee cap.

12. The invention according to claim 11 wherein said knee support is constructed from a fabric covered neoprene.

13. The invention according to claim 10 further including a third strap partially secured to and extending passed said first strap, a plurality of loop fasteners secured to said third strap and a plurality of hook fasteners being secured to said back of said second strap and being adapted to mate with said plurality of loop fasteners on said third strap for providing additional means for securing said support to the knee area.

* * * * *